(12) United States Patent
Poggio et al.

(10) Patent No.: US 6,334,352 B1
(45) Date of Patent: Jan. 1, 2002

(54) CONTROL DEVICE FOR A LINEAR OXYGEN SENSOR

(75) Inventors: Luca Poggio, Spinetta Marengo; Marco Secco, Nizza Monferrato; Piero Carbonaro, Turin; Daniele Ceccarini, Rimini, all of (IT)

(73) Assignee: Magneti Marelli S.p.A., Milan (IT)

( * ) Notice: Subject to any disclaimer, the term of this patent is extended or adjusted under 35 U.S.C. 154(b) by 0 days.

(21) Appl. No.: 09/438,476

(22) Filed: Nov. 12, 1999

(30) Foreign Application Priority Data

Nov. 13, 1998 (IT) .......................... B098A0626

(51) Int. Cl.[7] .............................. F01N 3/00
(52) U.S. Cl. ..................... 73/23.31; 73/118.1
(58) Field of Search ................ 73/23.31, 23.32, 73/116, 117.2, 117.3, 118.1

(56) References Cited

U.S. PATENT DOCUMENTS

| | | |
|---|---|---|
| 4,276,600 A | 6/1981 | Hartford et al. |
| 4,553,424 A * | 11/1985 | Sakurai et al. ............ 73/119 A |
| 4,651,699 A | 3/1987 | Ohtaki et al. |
| 5,795,545 A * | 8/1998 | Koripella et al. .......... 73/31.06 |
| 6,026,795 A * | 2/2000 | Poggio et al. |
| 5,832,724 A * | 11/2000 | Watanabe et al. |
| 6,167,697 B1 * | 1/2001 | Poggio et al. |

FOREIGN PATENT DOCUMENTS

EP          0 507 149 A1     10/1992

* cited by examiner

Primary Examiner—Eric S. McCall
(74) Attorney, Agent, or Firm—Venable; Robert Kinberg; Ashley J. Wells

(57) ABSTRACT

Control device for a linear oxygen sensor located in an exhaust pipe of an internal combustion engine in contact with exhaust gases in use, the control device including a linear oxygen sensor composed of at least one reference chamber for receiving a specified percentage of oxygen and being one of at least two types which differ in the way in which the at least one reference chamber receives oxygen; controller for exerting a control action on the linear oxygen sensor to generate an output signal (DIP) at an output representing a ratio of the exhaust gases and being composed of a programmable control device; and an operating unit for operating and programming the programmable control device to match the controller to the type of linear oxygen sensor to which it is connected.

20 Claims, 7 Drawing Sheets

CONTROL DEVICE FOR A LINEAR OXYGEN SENSOR

BACKGROUND OF THE INVENTION

1. Field of the Invention

The present invention relates to a control device for a linear oxygen sensor.

In particular, the present invention relates to a control device for a linear oxygen sensor known as a "UEGO" sensor (Universal Exhaust Gas Oxygen sensor), to which the following description will make explicit reference without thereby losing its general applicability.

The present invention is advantageously applicable in the field of motor vehicle manufacturing, in which there is a known use of a UEGO sensor located in the exhaust pipe of an internal combustion engine to obtain information on the composition of the exhaust gases.

2. Description of the Related Art

The UEGO sensor has two electrolytic cells sensitive to oxygen ions, called respectively the "pumping cell Ip" and the "sensing cell Vs", and a diffusion chamber located between these cells and capable of receiving part of the combustion gases leaving the engine. The UEGO sensor also has a reference chamber which is capable of containing a specified percentage of oxygen, namely, for example, a percentage of oxygen equal to that which the exhaust gases would have if the air/fuel ratio of the mixture supplied to the engine were stoichiometric. Alternatively, the reference chamber could contain a percentage of oxygen equal to that contained in the atmosphere.

The UEGO sensor requires the use of a controller, which is connected to the sensor by means of a connector, and is capable of controlling the current to the pumping cell Ip to exert a feedback control action on the sensor. In particular, the controller, on the basis of the difference between the percentage of oxygen present in the exhaust gases inside the diffusion chamber and the percentage of oxygen present in the reference chamber, regulates the current supplied to the pumping cell Ip in order to generate a mechanism for draining oxygen ions from the diffusion chamber to the external environment (or vice versa). This draining mechanism has the function of modifying the percentage of oxygen present in the diffusion chamber in such a way that the ratio between the percentages of oxygen in the diffusion chamber and in the reference chamber takes a specified value. This means that this draining mechanism has the role of adjusting the percentage of oxygen in the diffusion chamber to a specified value, in order, for example, to maintain the diffusion chamber in a state of stoichiometry.

The intensity of the control action, in other words the strength of the current supplied to the pumping cell Ip to maintain the stoichiometry in the diffusion chamber, is the information according to which the controller generates an output signal representing the ratio of the exhaust gases leaving the engine. This output signal, as is known, is used by the engine control unit, for example in order to correct the quantity of fuel to be supplied to the cylinders.

Two types of UEGO sensors are at present available on the market, and differ principally in the way in which the quantity of oxygen desired in the reference chamber is generated. In particular, one of the two types of UEGO sensor receives oxygen in the reference chamber directly from the external environment through the electrical cables which connect it to the connector, while the other type of UEGO sensor generates the oxygen itself in the reference chamber. This is done by making a polarization circuit of the corresponding controller send a polarization current to the sensing cell Vs, to generate a mechanism for draining oxygen from the exhaust gases in the diffusion chamber to the reference chamber.

In the present state of the art, both types of sensor have to be controlled by corresponding dedicated controllers, each of which has the limitation of not being capable of controlling a type of sensor different from that with which it is associated. This is because each of the two types of controller is physically constructed in such a way that it can only be connected to the type of sensor associated with it.

Moreover, each of the two types of control device has a drawback associated with the precision of the output signal.

This is because each controller of the known type has to be connected to a compensating resistance capable of compensating any losses of the current supplied to the pumping cell Ip, before the controller is installed in the vehicle. This compensating resistance, whose nominal value is indicated by the manufacturer of the sensor on completion of manufacture, is connected between two terminals of the connector, and, by interacting with the controller, intervenes actively in the generation of the output signal. In particular, the two terminals between which the compensating resistance is connected differ according to the type of sensor which is to be connected.

Unfortunately, the compensating resistance, being located in the engine compartment, is subjected to intense thermal stresses during the operation of the engine. Consequently, as the engine temperature varies and/or as a result of oxidation due to atmospheric agents, the compensating resistance may come to have values in relation to the controller which differ from the nominal value which ensures correct compensation. This means that the losses of driving current are not adequately compensated and the signal at the output of the controller does not accurately indicate the composition of the exhaust gases.

SUMMARY OF THE INVENTION

The object of the present invention is to provide a control device for a linear oxygen sensor, particularly a UEGO sensor, which overcomes the limitations of the known controllers, or in other words is capable of controlling both of the types of sensor mentioned above.

According to the present invention, a control device is provided for a linear oxygen sensor capable of being located in an exhaust pipe of an internal combustion engine, the control device comprising a controller of the sensor capable of exerting a control action on the sensor to generate at the output a signal representing the ratio of the exhaust gases; the sensor comprising at least one reference chamber capable of receiving a specified percentage of oxygen, and being one of at least two types which differ in the way in which the reference chamber receives the oxygen; and the control device being characterized in that the controller comprises programmable control means and in that it comprises an operating unit capable of operating and programming the said control means to match the controller to the type of sensor to which it is connected.

Conveniently, the control device for the sensor, where the sensor comprises a diffusion chamber capable of receiving the exhaust gases and a first and a second electrolytic cell sensitive to oxygen ions, the first of these cells being controllable with respect to current, is characterized in that the said control means comprise a feedback circuit capable of regulating the current sent to the first cell in accordance with the difference between the percentages of oxygen present in the diffusion chamber and in the reference chamber; the said feedback circuit comprising a means of generating the said output signal in accordance with the current sent to the first cell; the controller being connected to a compensating resistance capable of compensating the losses of the said sent current, and comprising an acquisition circuit capable of acquiring the value of the compensating resistance; the operating unit being capable of correcting the output signal of the controller in accordance with the acquired value of the compensating resistance, to generate a corresponding output signal which is truly representative of the ratio of the exhaust gases and which is independent of possible changes in the compensating resistance.

The control device is thus capable of compensating the losses of the driving current, by always using the acquired value of the compensating resistance. This ensures the generation of an output signal which is truly representative of the ratio of the exhaust gases and is independent of possible changes in the compensating resistance.

BRIEF DESCRIPTION OF THE DRAWINGS

The present invention will now be described with reference to the attached drawings, which illustrate a non-restrictive example of its embodiment in which.

DETAILED DESCRIPTION OF THE INVENTION

Figure 1:
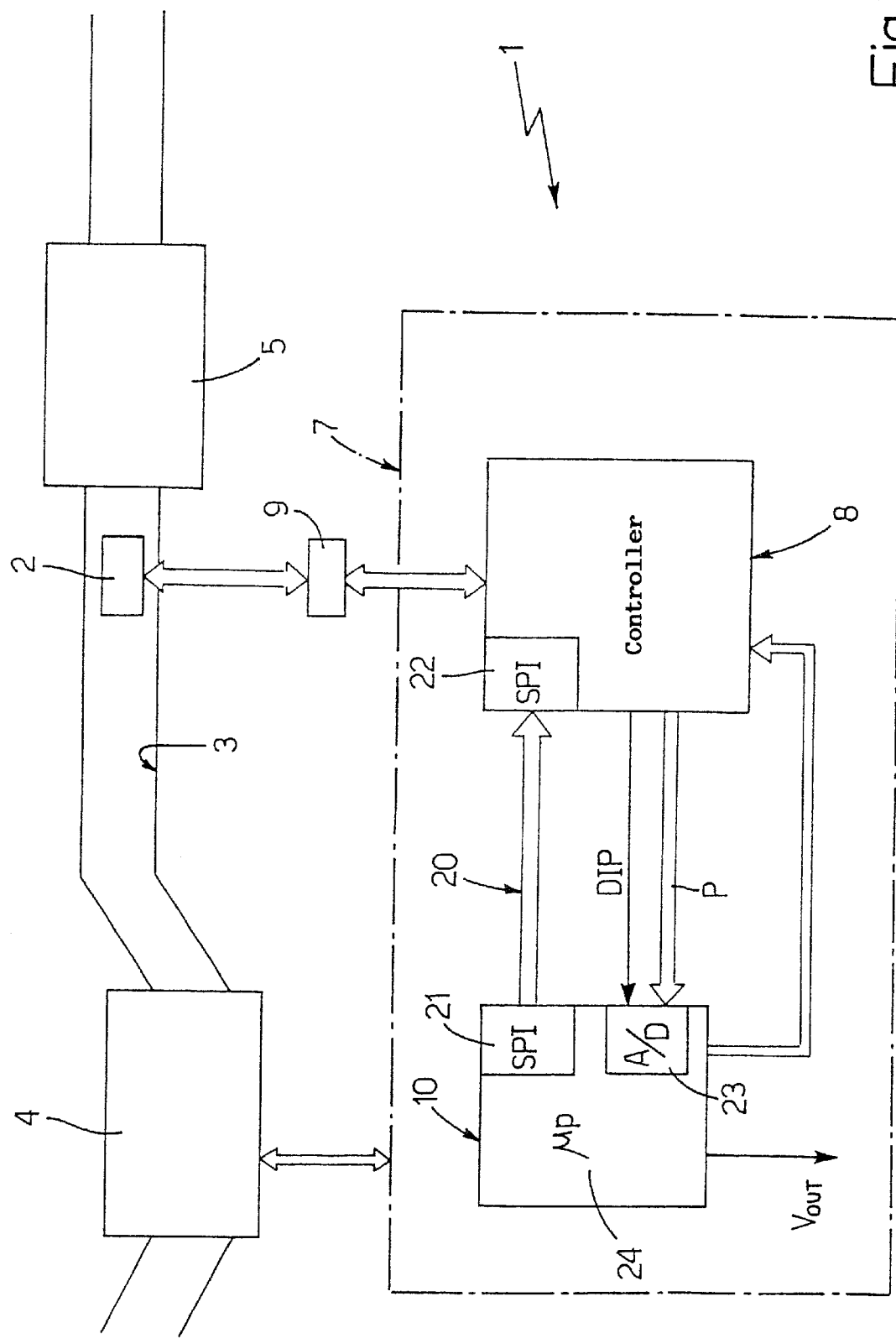
FIG. 1 shows schematically a device for controlling a UEGO sensor, made according to the principles of the present invention.

With reference to FIG. 1, the number 1 indicates, as a whole, a control device for a UEGO sensor 2 of a known type, which can be located in the exhaust pipe 3 of an internal combustion engine 4 to supply information on the stoichiometric composition of the combustion gases, and ultimately on the A/F (air/fuel) ratio of the mixture supplied to the engine 4.

In the illustrated example, the sensor 2 is located before a catalytic converter 5 capable of eliminating the polluting substances present in the combustion gases before they are emitted into the environment. In a variant which is not illustrated, the sensor 2 could be fitted after the catalytic converter 5 to supply information on the stoichiometric composition of the exhaust gases leaving the catalytic converter 4.

The control device 1 comprises a control unit 7 (shown schematically), which is responsible for the overall control of the engine 4.

The electronic control unit 7 comprises a controller 8 of the sensor 2 which is connected to the sensor 2 by a connector 9. As is specified more clearly below, the controller 8 is capable of controlling the sensor 2, and is capable of processing the information obtained from the sensor to generate at the output a signal DIP correlated with the quantity of oxygen present in the exhaust gases and, ultimately, with the A/F ratio.

The control unit 7 also comprises an operating and processing unit 10, which has the double function of operating and programming the controller 8 and processing the information from the output of the controller 8. In particular, the unit 10 is a microprocessor unit capable of processing the DIP output signal of the controller 8 to generate a signal Vout, which is proportional to the quantity of oxygen present in these gases, and is converted, in a known way, by the control unit into a parameter $\lambda$ indicating the ratio of the exhaust gases.

According to the present invention, the controller 8 (described below) has the distinctive characteristic of being capable of controlling UEGO sensors of different types. At the present time, motor vehicles are fitted with two types of UEGO sensor, which are illustrated schematically in FIGS. 2a and 2b and which, while they have many elements in common, differ in respect of some structural elements.

The two types of UEGO sensor will be described below, using the convention of indicating the first type of UEGO sensor with the reference 2a (FIG. 2a), indicating the second type of UEGO sensor with the reference 2b (FIG. 2b), and using common reference numbers to indicate structural parts common to the two sensors 2a, 2b.

Figure 2A:
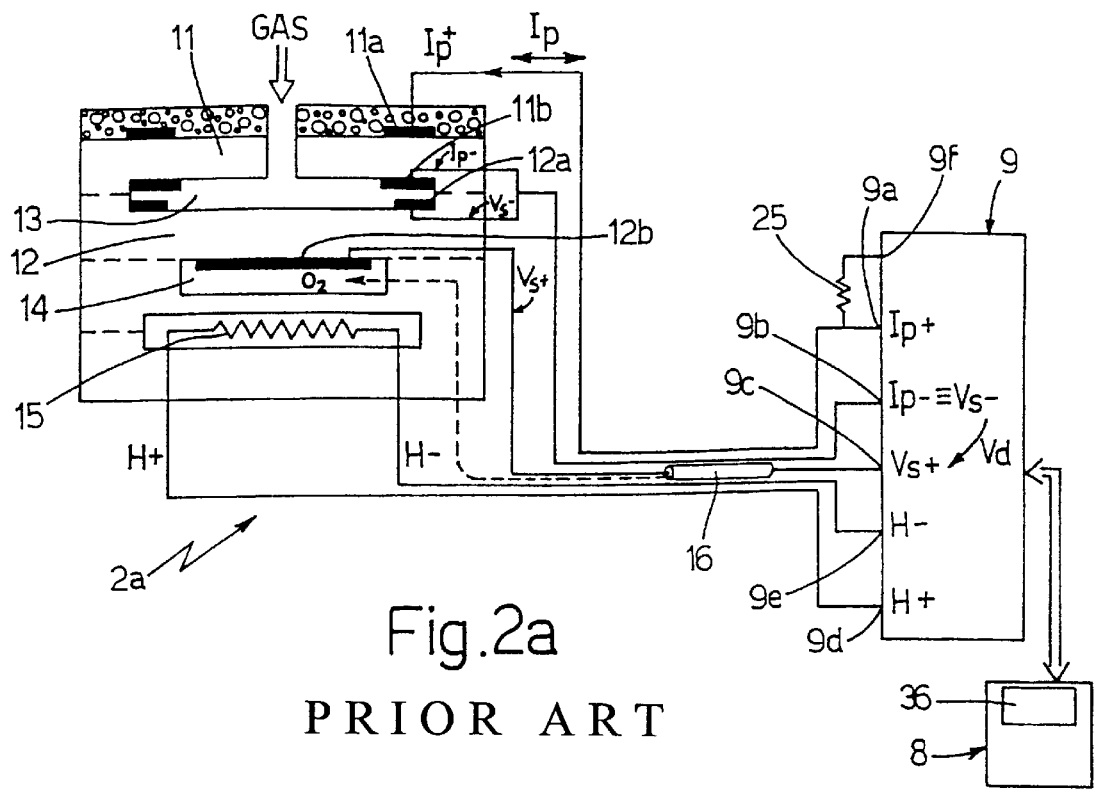
FIGS. 2a and 2b show schematically corresponding types of UEGO sensors used at present in internal combustion engines.
Figure 2B:
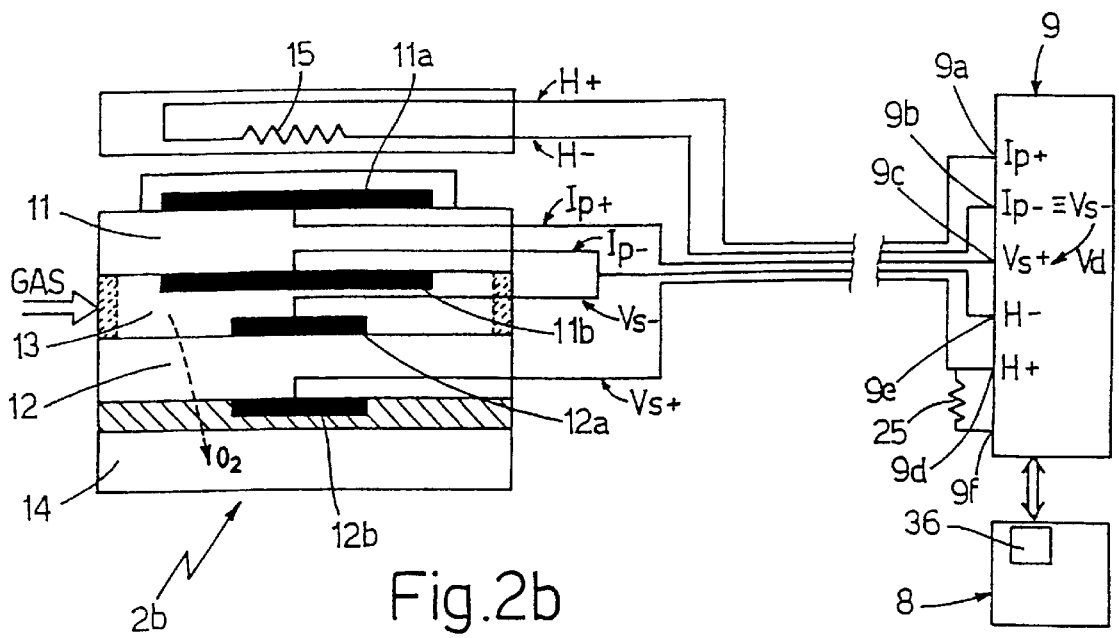

With reference to FIGS. 2a and 2b, each of the sensors 2a and 2b has two electrolytic cells 11 and 12 sensitive to oxygen ions, called the "pumping cell Ip" and the "sensing cell Vs" respectively, and a diffusion chamber 13, which is interposed between the cells 11 and 12, and is capable of receiving the exhaust gases leaving the engine.

Each of the sensors 2a and 2b is also provided with a reference chamber 14, which is placed on the opposite side of the diffusion chamber 13 with respect to the sensing cell 12, and is capable of containing a specified percentage of oxygen. In particular, the reference chamber 14 is capable of being brought to a reference state, in other words, for example, a state of stoichiometry characterized by the presence of a percentage of oxygen equal to that which the exhaust gases would have if the A/F ratio of the mixture supplied to the engine were stoichiometric. Alternatively, the reference state could be characterized by the presence of a percentage of oxygen equal to that present in the atmosphere.

At its terminals, the cell 11 has a pair of electrodes 11a and 11b connected electrically to corresponding terminals 9a, 9b of the connector 9, and also indicated below by Ip+ and Ip-. The cell 12, on the other hand, has at its terminals a pair of electrodes 12a and 12b (also indicated below by Vs- and Vs+), of which the electrode 12a is connected electrically to the electrode 11b of the cell 11, while the electrode 12b is connected to a terminal 9c of the connector 9.

Finally, each of the sensors 2a and 2b has a heating element which can be schematically represented as a heating resistance 15 connected between two further terminals 9d and 9e of the connector 9, and can be controlled in such a way that the sensor is heated to enable its temperature to be maintained within a specified range (generally approximately 780° C.).

The sensors 2a and 2b differ primarily in the way in which the oxygen is generated within the reference chamber 14. In the case of the sensor 2a, the reference chamber 14 is directly connected to the external environment, in other words to the atmosphere, by means of the connecting cable 16 which connects the electrode 12b of the sensor to the terminal 9c of the connector 9. The cross section of the connecting cable 16 is not completely occupied by the electrical connection, and has a free region through which oxygen is directed into the reference chamber 14.

Conversely, in the case of the sensor 2b, the oxygen which is directed into the reference chamber 14 is taken directly from the exhaust gases of the engine. This is done by sending a polarization current to the sensing cell 12, to provide a mechanism for draining oxygen ions from the diffusion chamber 13 to the reference chamber 14, by which mechanism the chamber 14 is brought into the said reference state.

The two sensors 2a and 2b can be controlled by the controller 8 according to a single operating principle, based on the feedback control of the pumping current Ip sent to the pumping cell 11.

This is because, when the sensor is active, a voltage signal Vd, whose value depends on the difference between the composition of the exhaust gases in the diffusion chamber 13 and the reference state of the reference chamber 14, is present between the terminals 9b and 9c, in other words at the terminals of the sensing cell 12. The controller 8 exerts a feedback control action designed to modify the composition of the gases inside the diffusion chamber 13. In particular, the controller 8 is capable of regulating the current Ip sent to the electrode 11a in accordance with the signal Vd, to establish a mechanism for draining oxygen ions from the diffusion chamber 13 to the external environment (and vice versa) in such a way as to maintain the ratio between the percentages of oxygen present in the diffusion chamber 13 and reference chamber 14 at a specified value.

The intensity of the control action, in other words the strength of the pumping current Ip, is the information according to which the controller 8 generates at its output the signal DIP representing the ratio of the exhaust gases.

As stated previously, the controller 8 (FIG. 1) can be configured to operate and control both types of UEGO sensor. In the illustrated embodiment, the controller 8 is connected to the control and processing unit 10 by a serial line 20, through which the controller 8 receives the information which permits matching to the type of sensor 2 connected to it. The unit 10 has a serial output interface 21 through which it sends commands and data to a serial input interface 22 of the controller 8.

Additionally, the output data from the controller 8, such as the signal DIP and other analog signals P (used for diagnosis of the sensor), are supplied to an analog/digital conversion circuit 23 of the unit 10 so that they can be converted to digital information which can be used directly within the microprocessor 24.

The operating unit 10 is also connected to the controller 8 by means of control lines in parallel and other analog signals.

As is known, the UEGO sensor 2 requires the use of a compensating resistance 25 (see FIGS. 2a and 2b), which is connected between two terminals of the connector 9, and is capable of compensating any losses of the pumping current Ip so that the signal Vout is always representative of the actual ratio of the exhaust gases. At the present time, the manufacturers of the sensor 2a and of the corresponding controller specify that the compensating resistance 25 is to be connected between the terminal 9a (Ip+) and a terminal 9f of the connector 9 (FIG. 2a), while the manufacturers of the sensor 2b and of the corresponding controller specify that the compensating resistance 25 is to be connected between the terminal 9d (H+) and the terminal 9f of the connector 9 (FIG. 2b).

The nominal value of the compensating resistance 25 is specified on completion of the manufacture of the sensor 2, following functional verifications conducted to test the efficiency of the sensor.

According to the present invention, the controller 8 is made in such a way that it can carry out the control operation both in the case in which the resistance 25 is connected between the terminals 9a and 9f and in the case in which the resistance 25 is connected between the terminals 9d and 9f. As will be indicated below, this is because the controller 8 has a circuit for acquiring the value of the compensating resistance 25 which is capable of storing the value of this resistance, so that the DIP signal correction operations are always carried out with the same stored value of the resistance, independently of the real value of the physical resistance, which is known to be subject to thermal and/or atmospheric stresses capable of changing its nominal value.

Figure 3:
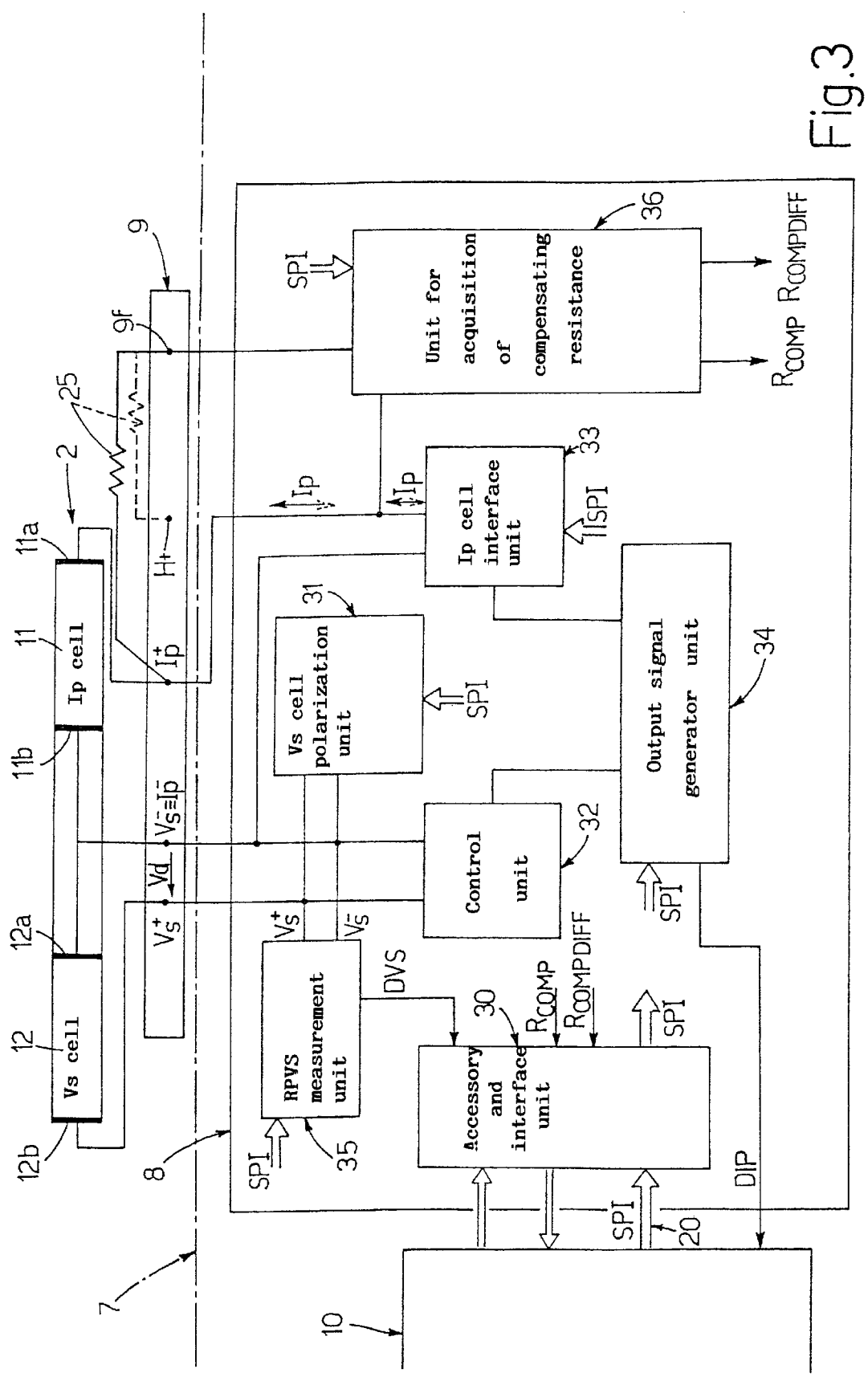
FIG. 3 is a functional diagram of a controller forming part of the device shown in FIG. 1.
Figure 4:
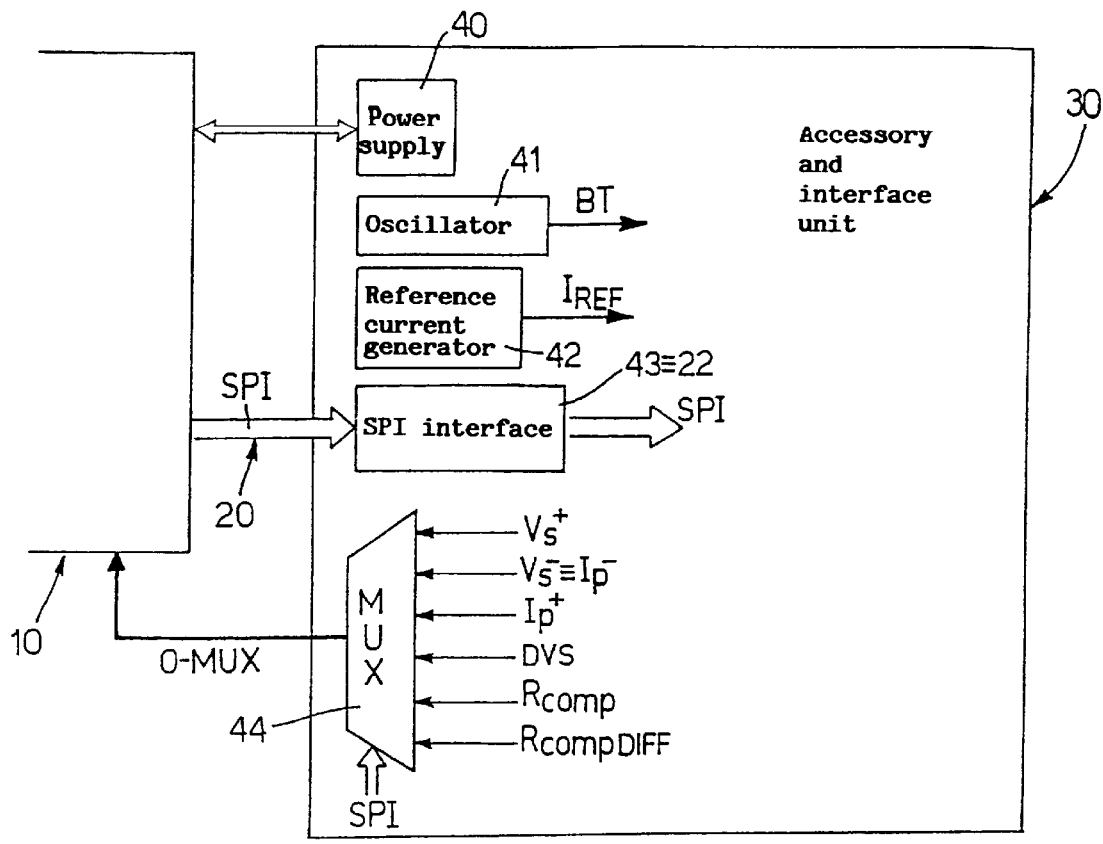
FIG. 4 shows a first functional unit forming part of the controller in FIG. 3.

The controller 8 will now be described in detail with reference to FIG. 3.

The controller 8 comprises seven functional units, indicated by the reference numbers 30, 31, 32, 33, 34, 35, 36 and interacting with each other .

The functional unit 30 is capable of forming an interface between the controller 8 and the control and processing unit 10, and, as will be described, acts as an accessory unit to the other units. This is because the unit 30 not only supplies the other units with the information from the unit 10, but also provides them with physical values (for example, reference currents) which will be used within the units themselves.

The functional unit 31 is a unit which can polarize the sensing cell 12 of the sensor 2 in a selective way if the sensor is of the type shown in FIG. 2b, in other words if the cell has to be polarized for self-generation of the oxygen in the reference chamber 14. In other words, depending on the type of sensor 2 which is connected to the controller 8, the unit 10, through the serial line 20, causes the unit 31 to polarize the cell 12 (sensor 2b), or keeps the polarization of the cell 12 disabled (sensor 2a).

The unit 32 is a control unit for the sensing cell 12 of the sensor 2, and is capable of processing the signal Vd at the terminals of the cell 12 to execute the said feedback control action, and to supply at the output a control parameter VAD which identifies the pumping current Ip to be sent to the pumping cell 11.

The unit 33 is capable of forming an interface with the pumping cell 11, and in particular is capable of controlling the current Ip according to the result of the processing operation carried out by the control unit 32.

The unit 34 is capable of generating the output signal DIP according to the result of the processing operation carried out by the control unit 32, and therefore, ultimately, according to the current strength required to maintain stoichiometry in the diffusion chamber 13. In other words, this unit 34 is capable of carrying out a kind of measurement of the pumping current Ip to supply the signal DIP at the output, and, as will be shown subsequently, is capable of being configured by the unit 10 in such a way that the signal DIP represents the ratio of the exhaust gases in a programmable and modifiable range of values. This means that the controller 8 generates an output signal DIP which, in a specified voltage range (e.g. 0–5 volts), can represent the variations of the ratio at discharge relative to a range of amplitude which is also programmable according to the requirements in terms of resolution.

The unit 35 is a unit capable of measuring the internal resistance RPVS of the sensing cell 12, the value of this internal resistance RPVS being indicative of the temperature of the sensor and being used to control the heating element of the sensor 2, in other words to regulate the current sent to the heating resistance 1a (FIGS. 2a, 2b). Finally, the unit 36 is capable of executing the said operation of acquiring the value of the compensating resistance 25 which must be connected between the two terminals of the connector 9 (see FIGS. 2a and 2b)1 In other words, this unit 36 is capable of enabling the operating unit 10 to sample and store the value of the compensating resistance 25 in such a way that the unit 10 can always correct the signal DIP with the same parameter, thus compensating for the said losses of the driving current Ip of the cell 11. This acquisition takes place independently of the configuration of the connection of the compensating resistance 25 to the connector 9 (see FIGS. 2a and 2b).

The units 30, 31, 32, 33, 34, 35, 36 forming the controller 8 will now be described in detail with reference to FIGS. 4 to 9.

The unit 30 (FIG. 4) has a power supply circuit 40 of a known type, which interacts with the operating unit 10 to receive a plurality of signals (e.g. battery voltage, voltage stabilized at 5 volts, and earths), and which is capable of supplying the power supply voltages and the earth references for the other units 31 to 36.

The unit 30 has an oscillating circuit 41 of a known type, capable of supplying at its output a clock signal BT which is used by the units which have to carry out time-based measurement or synchronization (for example, the said unit 34 for measuring the internal resistance RPVS of the cell 12).

The unit 30 is also provided with a current generator circuit 42 (of a known type), which is capable of generating a stable and precise reference current IREF, and which has the function of making it available to the other units to enable them to carry out the operations associated with them.

Finally, the unit 30 has two further circuits, indicated by the reference numbers 43 and 44, of which the circuit 43 forms the serial interface 22 of the controller 8, and is capable of converting the codes received from the microprocessor 24 into signals SPI for operating and programming the other units 31 to 36. The circuit 44 is a selector circuit which, in this specific case, consists of a multiplexer having at least six inputs, selection inputs formed by the signals SPI from the unit 10, and an output O-Mux connected to the unit 10. In particular, the six inputs of the multiplexer receive the following signals: the voltage Vs+ of the cell 12, the voltage Vs– of the cell 12, the current Ip+ supplied to the cell 11, the voltage DVS at the terminals of the sensing cell 12, and two signals RCOMP and RCOMPDIFF (the nature of which is clearly described below) indicating the value of the compensating resistance 25 in cases in which the controller 8 is connected to the sensor 2b or to the sensor 2a.

The multiplexer 44 is capable of transferring the selected input to the O-Mux output, according to the requests sent by the unit 10 by means of the signals SPI, in such a way as to supply it to the operating unit 10 and to make it possible to carry out diagnostic operations relating to the functional state of the sensor 2 and/or acquisitions by the control unit of the value of the compensating resistance 25.

The unit 31 for polarizing the sensing cell 12 receives at its input the signals SPI from the operating unit 10, and, according to these signals, is capable of polarizing the cell 12 if the sensor 2 connected to the connector 9 is the sensor 2b.

Figure 5:
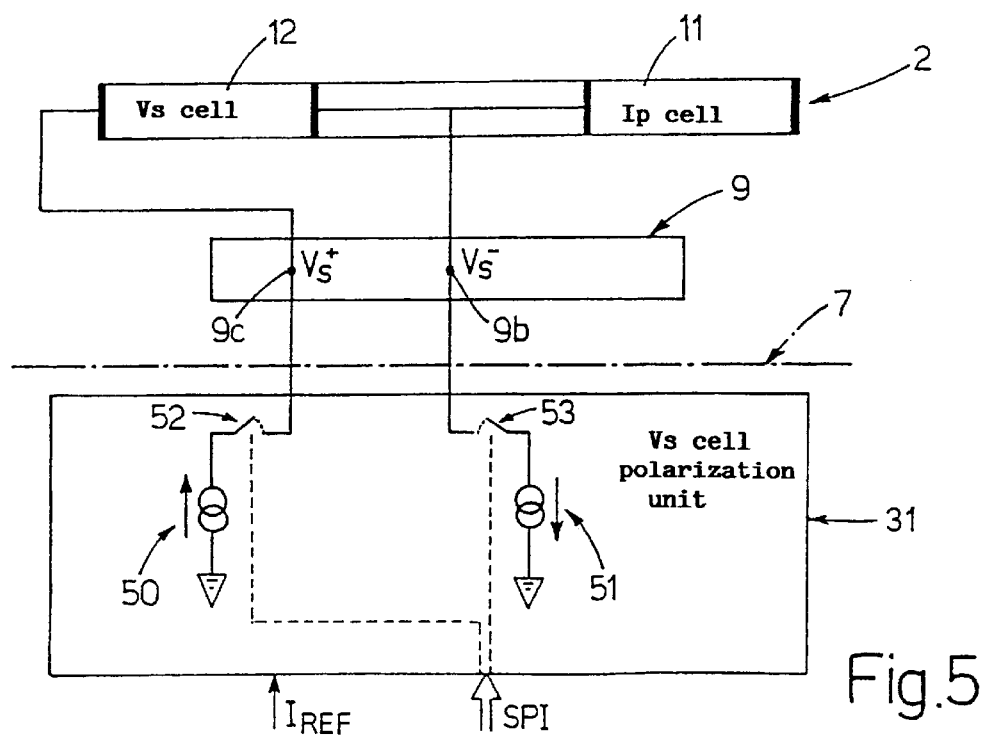
FIG. 5 shows schematically a second functional unit forming part of the controller.

FIG. 5 shows schematically a possible embodiment of the polarization unit 31. In this embodiment, the unit 31 consists of two polarization current generators, indicated by the reference numbers 50 and 51, of which the generator 50 is connected to the terminal 9c of the connector 9 (and consequently to the electrode 12a (Vs+) of the cell 12) through a switch 52 operated by the signals SPI. The generator 51 is connected to the terminal 9b of the connector 9 (and consequently to the electrode 12b (Vs–≡Ip–) of the cell 12) through a switch 53 which is also operated by the signals SPI. The polarization current from the generators 50 and 51 is obtained directly from the reference current IREF at the output of the circuit 42 of the unit 30. In operation, if the sensor 2b is connected, the operating unit 10, by means of the signals SPI, causes the switches 52 and 53 to close in such a way as to generate the polarization current in the sensing cell 12 and to generate the said mechanism for draining the oxygen ions from the exhaust gases to the reference chamber 14. Conversely, if the sensor 2a is connected, the operating unit 10 keeps the switches 52 and 53 open, thus preventing the polarization of the cell 12.

A schematic embodiment of the units 32, 33, 34 will now be described with reference to FIG. 6.

The control unit 32 comprises a differential to amplifier 60 whose inputs are connected to the terminals 9b and 9c of the connector 9 to receive the voltage signal Vd, and is capable of supplying the amplified signal Vd to a subtraction input 61a of an addition node 61. In particular, the amplified signal Vd will have a reference value (approximately 450 mV for example) if gases originating from the combustion of a stoichiometric mixture are present in the diffusion chamber 13, while it has a value greater than the reference value (or smaller than the reference value) if gases originating from the combustion of a rich mixture (or lean mixture) are present therein.

The addition node 61 has an addition input 61b to which is supplied a reference signal VdRIF, which represents the reference (or "set point") for the amplified signal Vd, and which is equal to the amplified value of the signal Vd if the exhaust gases entering the diffusion chamber 13 originate from the combustion of a stoichiometric mixture. In other words, the reference signal VdRIF represents the value of the potential differential across the terminals of the sensing cell 12 if the ratio between the percentage of oxygen in the diffusion chamber 13 and that in the reference chamber 14 is equal to the said specified value.

The node 61 generates at its output an error signal VERR, which consists of the difference between the reference signal VdRIF and the amplified signal Vd, and represents the error between the voltage present at the terminals of the sensing cell 12 in stoichiometric conditions and that which is actually measured at the terminals of the cell 12.

The error signal VERR is supplied to a processing circuit 62 capable of processing it to supply at the output the control parameter VAD which identifies the pumping current Ip to be sent to the pumping cell 11. In the illustrated example, the processing circuit 62 consists of a PID controller of a known type, capable of executing a proportional integral derivative (PID) transformation of the signal VERR, but the transformation of the signal VERR may be different from that illustrated.

Figure 6:
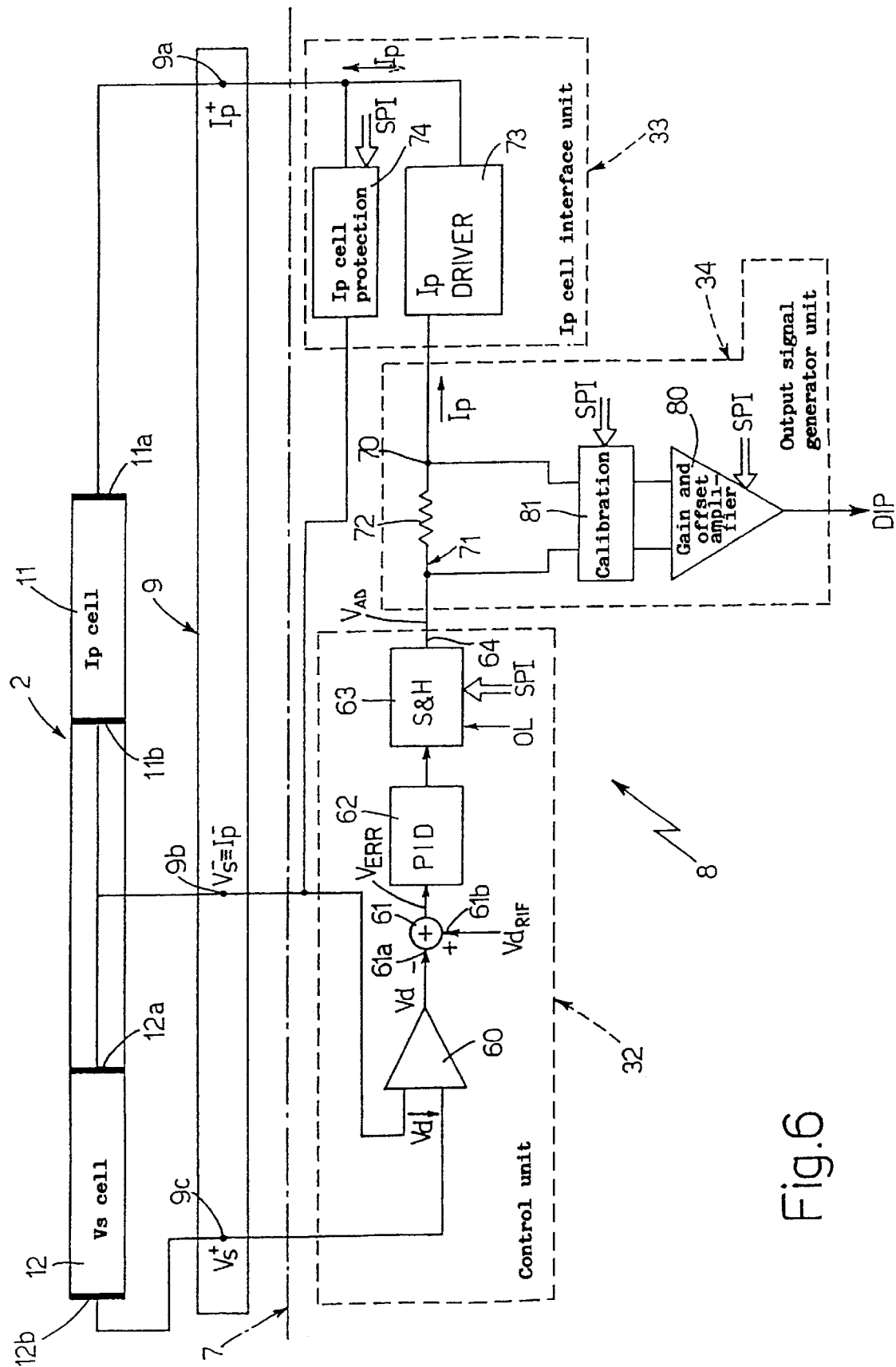
FIG. 6 shows schematically three functional units forming part of the controller.

As shown in FIG. 6, the output of the processing circuit 62 is supplied to a sampling and holding circuit 63 (in the form of a "Sample & Hold" device), the operation of which is clearly described below. The circuit 63 is operated by means of the signals SPI, and has an output terminal 64 at which the parameter VAD forming the output of the control unit 32 is present.

The output VAD of the unit 32 is then supplied, through an electrical connection 71 in which a precision resistance 72, called the sensing resistance, is connected, to the input 70 of the interface unit 33 connected to the pumping cell 11. Thus the voltage output VAD of the unit 32 is converted into a current signal representing the pumping current Ip to be supplied to the cell 11.

The unit 33 has a driver circuit 73 (shown schematically) which receives the said current signal at its input, and is capable of sending the current Ip to the pumping cell 11. This driver circuit 73 (of a known type) is commonly described as an "Ip-driver", and in structural terms it may be formed by a follower in such a way that the current flowing through the precision resistance 72 is exactly equal to the driving current Ip sent to the cell 11. According to the above description, the output parameter VAD of the control unit 32 is the input according to which the driver circuit 73 sends the current Ip in order to regulate the mechanism for draining oxygen ions from the diffusion chamber 13 to the external environment (or vice versa) in an attempt to establish stoichiometry in the chamber 13.

In this way, a feedback control system which tends to cancel the error signal VERR is provided. In this feedback control system, if the exhaust gases entering the diffusion chamber 13 are derived from the combustion of a lean mixture, the signal VERR is greater than zero, and the PID controller operates the driver circuit 73 in such a way that a current Ip capable of generating a flow of oxygen ions from the chamber 13 towards the external environment is sent to the cell 11. Thus the feedback control system tends to return the chamber 13 to a stoichiometric state. Conversely, if the exhaust gases have a low oxygen content, in other words if they are derived from the combustion of a rich mixture, the signal VERR is less than zero, and the PID controller operates the driver circuit 73 in such a way that a current Ip capable of generating a flow of oxygen ions from the exterior towards the diffusion chamber 13 is sent to the cell 11. Thus the feedback control system tends to return the chamber 13 to a stoichiometric state.

The interface unit 33 connected to the pumping cell 11 also has a protection circuit 74 capable of preventing the voltage at the terminals of the cell 11 from exceeding a specified threshold value, beyond which the sensor 2 may be damaged. The circuit 74 is enabled by the operating unit 10 through the signals SPI.

According to the illustration in FIG. 6, the unit 34 generating the output signal DIP of the controller 8 has a differential voltage amplifier 80, which is connected to the terminals of the sensing resistance 72 to measure the voltage drop across it and, consequently, to measure the pumping current Ip supplied to the cell 11.

According to the present invention, the amplifier 80 is a programmable gain and offset amplifier, and is capable of amplifying the input voltage for values programmable by means of the signals SPI. The output signal DIP of the controller 8 is present at the output of the amplifier 80, and this signal DIP is therefore a function of the strength of the current which is applied to maintain stoichiometry in the diffusion chamber 13. Since the gain and offset of the amplifier 80 are programmable, it is possible to measure currents Ip which have different dynamic characteristics, at different resolutions. This means that the controller 8 is capable of providing an output signal DIP which, in a predetermined range of voltages (e.g. 0–5 V), represents the variations of the ratio in the exhaust over a programmable range of values which can be modified according to requirements.

Figure 7:
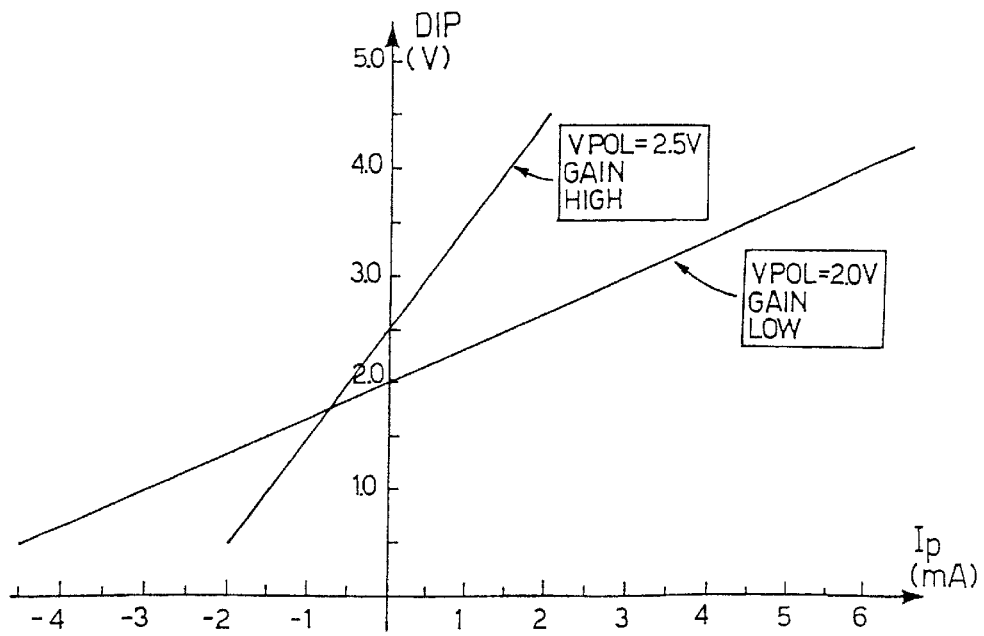
FIG. 7 shows the graph of two possible output characteristics of the controller.

FIG. 7 shows two possible graphs of the characteristic expressing the output signal DIP as a function of the strength of the pumping current Ip, these graphs being obtained with different gain and offset values of the amplifier 80.

Since the precision required in the measurement of the current Ip is very high, the unit 34 also has a calibration circuit 81 for the amplifier 80, for evaluating the errors introduced by the amplifier 80. This calibration circuit 81 is also activated by the operating unit 10 by means of the signals SPI, and, when activated, short-circuits the inputs of the amplifier 80 and connects them to the offset voltage. In this way, the measurement of the output of the amplifier 80 provides information on the measurement errors.

Figure 8:
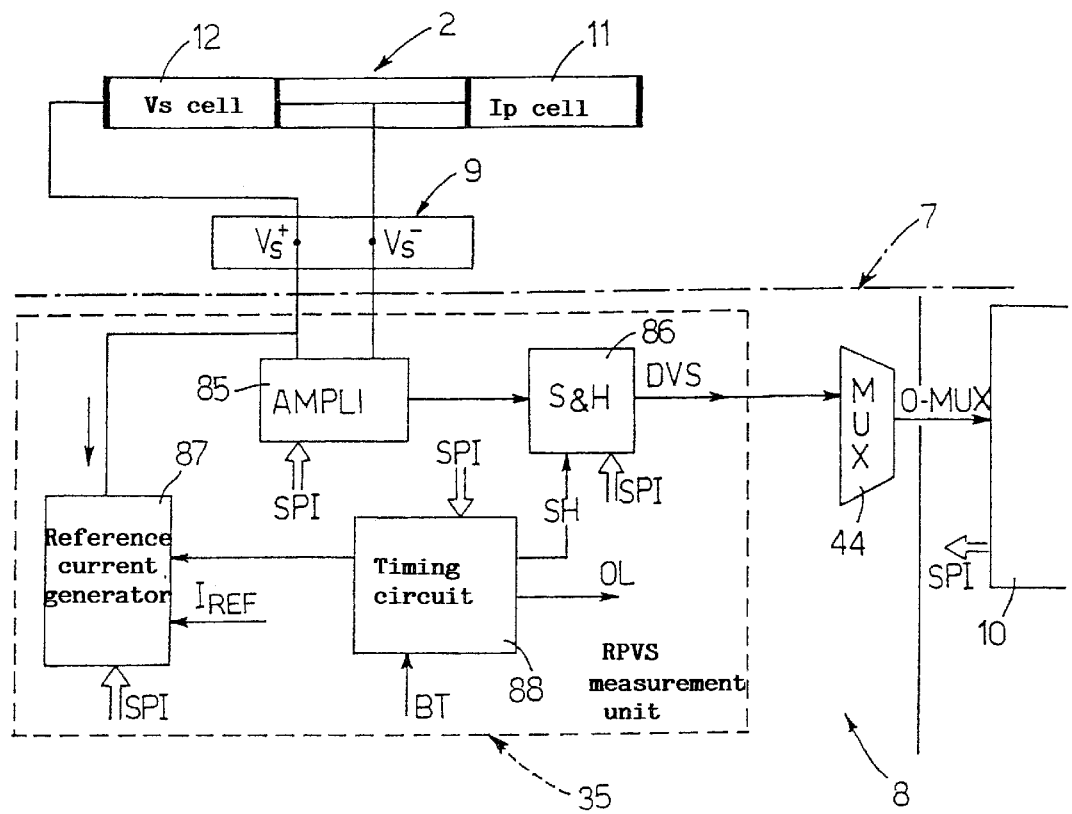
FIG. 8 shows a diagram of a sixth functional unit of the controller.

The unit 35 for measuring the internal resistance RPVS of the sensing cell 12 will now be described with reference to FIG. 8. The internal resistance RPVS is measured by forcing a known reference current in the cell 12 and measuring the voltage drop across the terminals of the cell 12.

For this purpose, the unit 35 has a differential amplifier 85 whose inputs are connected to the electrodes 12a and 12b of the sensing cell 12 in such a way that the voltage drop Vd across the terminals of the cell 12 is present between them. The output of the amplifier 85 is connected to a sampling circuit 86 (in the form of a "Sample & Hold" circuit), whose output represents the said signal DVS at the input of the multiplexer 44 of the unit 30. The unit 35 also has a current generator circuit 87 connected to the electrode Vs+ of the cell 12 and capable of being operated by the unit 10 (by means of the SPI signals) to generate a reference current in the sensing cell 12. In particular, the reference current is obtained from the current IREF made available by the generator 42 of the unit 30, and its strength can be regulated according to the type of sensor 2 which is connected.

Finally, the unit 35 has a timer circuit 88 capable of generating the timings required to synchronize the operations which contribute to the measurement of the internal resistance RPVS. This circuit 88 receives at its inputs both the clock signal BT from the circuit 41 (FIG. 4) and the command, using the signals SPI, for enabling the measurement of the resistance RPVS.

The circuit 88 is capable of operating the circuit 87 to regulate the timing of the supply of the reference current to the cell 12, and is also capable of operating the sampling circuits 86 and 63, by means of corresponding signals SH and OL indicating the sampling instants.

In use, the operating unit 10 operates the timer circuit 88 to enable the measurement of the internal resistance RPVS. First, the unit 10 causes the voltage DVS at the terminals of the cell 12 to be acquired. Then the circuit 88 operates the sampling circuit 63 by means of the signal OL so that the output parameter VAD of the control unit 32 is stored. The circuit 88 then enables the current generator circuit 87 to operate in such a way that the reference current is sent to the sensing cell 12, thus perturbing the state of the cell 12. When this has been done, the voltage at the terminals of the sensing cell 12, due additionally to the reference current, are present at the terminals of the amplifier 85. Finally, the timer circuit 88 operates the sampling circuit 87 to "freeze" the amplified voltage present at the terminals of the cell 12, in other words the signal DVS. At this point, the operating unit 10 may operate the multiplexer 44 to receive the frozen voltage DVS. From the values of the voltage DVS acquired before and after the reference current was sent to the cell 12, the unit 10 can determine the voltage drop in the cell 12 which is due solely to the reference current, and, since the value of the reference current is known, can easily calculate the internal resistance RPVS.

It should be emphasized that the storing of the output parameter VAD by the sampling circuit 63 makes it possible to have no changes in the output signal DIP of the controller 8 during the operations designed to permit the measurement of the internal resistance RPVS of the sensing cell 12.

The unit 36 for acquiring the compensating resistance 25 connected to the connector 9 will now be described with reference to FIG. 9.

Figure 9:
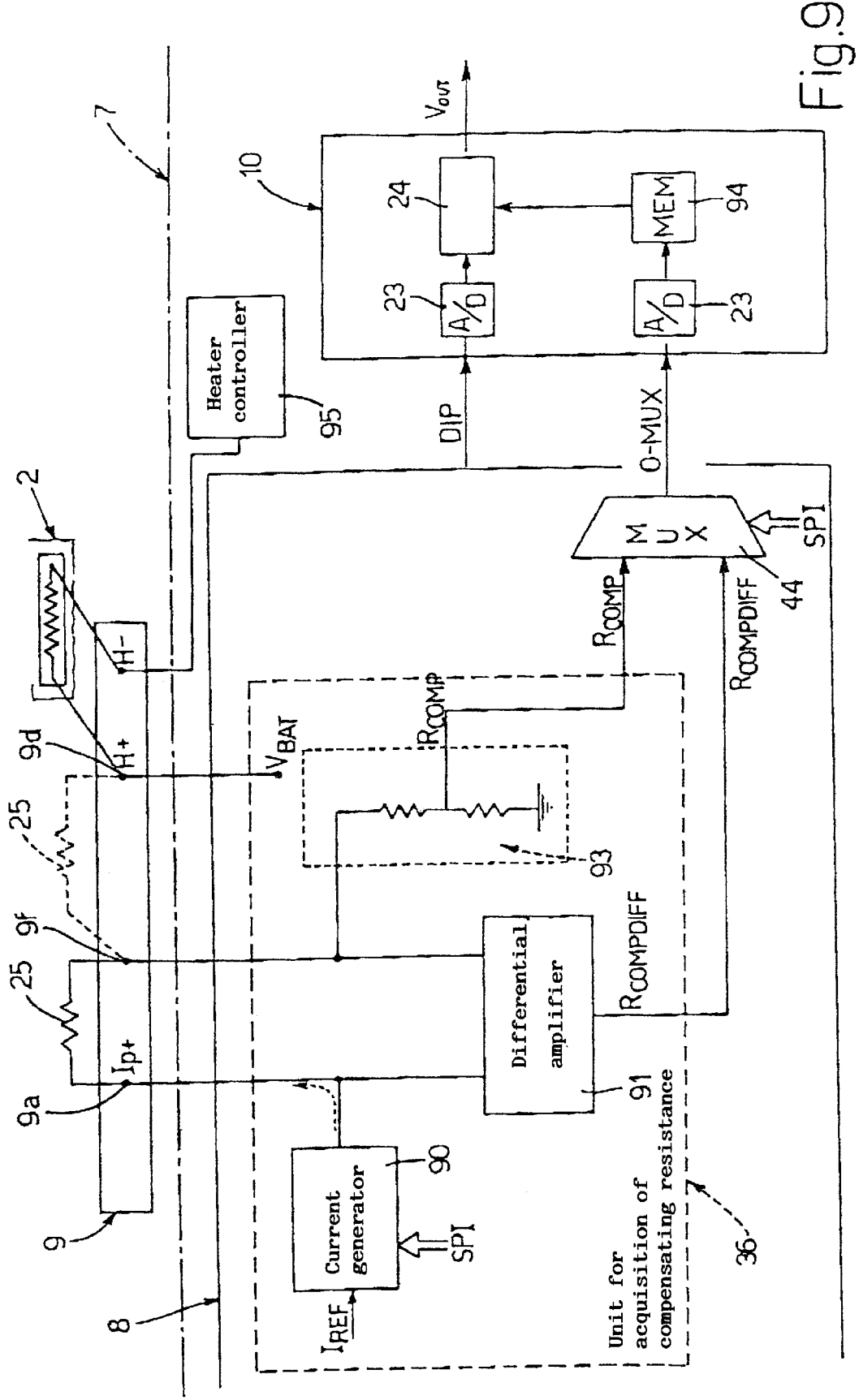
FIG. 9 shows a diagram of a seventh functional unit of the controller.

In FIG. 9, the connection of the compensating resistance 25 to the connector is shown in continuous lines for the case in which the sensor 2a is connected, while the connection of the resistance 25 is indicated in broken lines for the case in which the sensor 2b is connected (see also FIGS. 2a, 2b).

The unit 36 is capable of controlling the acquisition of the resistance 25 independently of the type of connection.

The unit 36 has a current generator circuit 90 which is connected to the terminal 9a (Ip+) of the connector 9, and which can be operated by the unit 10, by means of the signals SPI, to send a reference current to the resistance 25. The reference current is obtained from the reference current IREF made available by the circuit 42 (FIG. 4), and the strength of the reference current is programmable by means of the signals SPI.

The unit 36 also has a differential amplifier 91 whose inputs are connected to the terminals 9a and 9f of the connector 9, in other words to the terminals of the resistance 25 if the UEGO sensor of type 2a is connected. This amplifier 91 is capable of amplifying the voltage present at the input to supply at the output a signal RCOMPDIFF indicating the compensating resistance 25. The signal RCOMPDIFF is then supplied to the input of the multiplexer 44.

In use, if the compensating resistance 25 is connected between the terminals 9a and 9f, the operating unit 10 activates the circuit 90 in such a way that the reference current passes through the resistance 25. The differential amplifier 91 amplifies the voltage at the terminals of the resistance 25, and supplies the signal RCOMPDIFF, representing the resistance 25, to the multiplexer 44. At this point, the operating unit 10 selects the input of the multiplexer 44 corresponding to the signal RCOMPDIFF in such a way that the signal is received in the analog/digital converter 23 (FIG. 1). The operating unit 10 can derive the value of the compensating resistance 25 from the known value of the reference current sent to the resistance 25 and the received signal RCOMPDIFF.

However, if the compensating resistance 25 is connected between the terminals 9d and 9f, its value is acquired in a different way. The terminal 9d is connected to the power supply voltage (battery voltage, VBAT), while the terminal 9f is connected to a voltage divider 93 whose output is the signal RCOMP which represents the resistance 25 and is supplied to the input of the multiplexer 44. The voltage divider 93 has the function of matching the level of the signal RCOMP to the dynamics of the input of the multiplexer 44.

The resistance 25, connected to the power supply voltage, thus has a current passing through it, and the voltage signal RCOMP is generated. This signal RCOMP is acquired by the operating unit 10 by the selection of the corresponding input in the multiplexer 44. The unit 10 can then determine the value of the compensating resistance 25 from the value of the power supply voltage VBAT, the signal RCOMP and the values of the resistances of the divider 93.

It should be noted that, in the latter case, the current generator circuit 90 is kept disabled by the unit 10.

In both of the above cases, the operation of acquiring the value of the compensating resistance 25 is carried out when the engine 4 is started. The acquired value of the compensating resistance is stored by the unit 10 in a memory unit 94, so that it can be used to provide the said compensation of the losses of the pumping current Ip.

This is done by using the stored value of the compensating resistance 25 to correct the output signal DIP of the controller 8. This correction is carried out by the microprocessor 24, and makes it possible to generate a signal VOUT which is truly indicative of the ratio of the exhaust gases.

In this way, during the operation of the engine, the compensation of the losses of the pumping current Ip is always carried out on the basis of the acquired and stored value of the resistance 25. Therefore, although the resistance 25 may be subjected to thermal stresses which change its value from the nominal value, the signal VOUT is not affected by the changes in the resistance 25 and continues to represent the actual composition of the exhaust gases.

Finally, the control device 1 has a circuit 95 (FIG. 9) for controlling the heating resistance 15 of the sensor 2 (FIGS. 2a and 2b). As stated previously, the resistance 15 is connected to the terminals 9d and 9e (in other words, H+ and H−) of the connector 9, whose terminal 9d is connected to the battery voltage VBAT.

The circuit 95 for controlling the resistance 15 is a circuit of a known type, and therefore it will not be described in detail. This control circuit 95 is connected to terminal 9e (H−), and is capable of regulating the current passing through the heating resistance 15, to bring the sensor rapidly to the required temperature and to keep it within a range of maximum efficiency (for example, approximately 780° C.) during the operation of the engine.

The control device illustrated above has considerable advantages compared to the known control devices. In the first place, the control device 1 can be used to control sensors 2 of different types, and generates an output signal VOUT which is independent of the variations of the compensating resistance 25.

Secondly, the programmability of the unit 34 for generating the signal DIP makes it possible to generate an output signal representing the variations of the ratio of the exhaust gases within a programmable and modifiable range of values. On the other hand, every known type of controller provides output signals representing the ratio $\lambda$ of the exhaust gases solely within a single specified range of values, for example $\lambda \in (0.7, 1.2)$, while it does not provide significant information outside this range.

Moreover, the programmability of the unit 35 for measuring the internal resistance RPVS makes it possible to measure this internal resistance RPVS with both types of sensor, which, as is known, require different reference currents in their sensing cells 12.

What is claimed is:

1. Control device for a linear oxygen sensor located in an exhaust pipe of an internal combustion engine in contact with exhaust gases in use, the control device comprising:

a linear oxygen sensor comprising at least one reference chamber for receiving a specified percentage of oxygen and being one of at least two types which differ in the way in which the at least one reference chamber receives oxygen;

controller for exerting a control action on the linear oxygen sensor to generate an output signal (DIP) at an output representing a ratio of the exhaust gases and being comprised of programmable control means; and an operating unit for operating and programming the programmable control means to match the controller to the type of linear oxygen sensor to which it is connected.

2. The control device according to claim 1, wherein the linear oxygen sensor further comprises a diffusion chamber for receiving the exhaust gases; and first and second electrolytic cells which are sensitive to oxygen ions, the first electrolytic cell being controllable with respect to current, wherein the programmable control means comprises a feedback circuit for regulating the current (Ip) sent to the first electrolytic cell in accordance with a difference between percentages of oxygen present in the diffusion chamber and in the at least one reference chamber;

wherein the feedback circuit comprises means for generating the output signal (DIP) in accordance with the current (Ip) sent to the first electrolytic cell;

wherein the controller is connected to a compensating resistance for compensating the losses of the current (Ip) sent, and comprises an acquisition circuit for acquiring a value (RCOMP; RCOMPDIFF) of the compensating resistance; and wherein the operating unit corrects the output signal (DIP) of the controller in accordance with the value (RCOMP; RCOMPDIFF) of the compensating resistance to generate a corresponding output signal (VOUT) which is truly representative of the ratio of the exhaust gases and which is independent of possible changes in the compensating resistance.

3. The control device according to claim 2, wherein the programmable control means comprises polarizing means for polarizing the second electrolytic cell which can be activated selectively by the operating unit according to the type of sensor connected to the controller and which polarizes the second electrolytic cell to produce the oxygen in the at least one reference chamber.

4. The control device according to claim 3, wherein the polarizing means comprises at least one polarization current generator connected to the second electrolytic cell and switch means interposed between the at least one polarization current generator and the second electrolytic cell for sending the polarization current in a selective way to the second electrolytic cell.

5. The control device according to claim 2, wherein the polarizing means for generating the output signal (DIP) of the controller is programmable by the operating unit in such a way that the output signal (DIP) indicates variation of the ratio of the exhaust gases within a range of values which is programmable and can be modified as desired.

6. The control device according to claim 2, wherein the linear oxygen sensor generates a first signal (Vd) representing a difference between percentages of oxygen present in the diffusion chamber and in the at least one reference chamber, and wherein the feedback circuit comprises:

processing means for receiving and processing the first signal (Vd) to generate at the output an output parameter (VAD) which identifies the current (Ip) which drives the first electrolytic cell; and driving means for sending the current (Ip) to the first electrolytic cell in accordance with the output parameter (VAD) of the processing means; and means for generating the output signal (DIP) of the controller in accordance with the output parameter (VAD) of the processing means.

7. The control device according to claim 6, wherein the output parameter (VAD) of the processing means is supplied to an input of the driving means through a connecting line having a precision resistance through which current sent by the driving means to the first electrolytic cell can pass, the connecting line being part of the means for generating the output signal (DIP) of the controller.

8. The control device according to claim 7, wherein the means for generating the output signal (DIP) of the controller comprises first amplifier means with programmable gain and offset connected to terminals of the precision resistance to amplify the voltage present at the terminals of the precision resistance.

9. The control device according to claim 8, wherein the means for generating the output signal (DIP) of the controller further comprises means for calibrating the first amplifier means to evaluate errors introduced by the first amplifier means in the generation of the output signal (DIP) of the controller.

10. The control device according to claim 7, wherein the driving means comprises a driver circuit for sending to the first electrolytic cell exactly the current which passes through the precision resistance.

11. The control device according to claim 7, wherein the processing means for receiving and processing the first signal (Vd) comprises:

second amplifier means for amplifying the first signal (Vd);

means for generating a reference signal (Vdrif) indicating an objective value of the amplified first signal (Vd);

comparing means for comparing the reference signal (Vdrif) with the amplified first signal (Vd) and for generating an error signal (VERR); and a processing circuit for receiving at an input the error signal (VERR) and for processing the error signal (VERR) to generate the output parameter (VAD) of the processing means.

12. The control device according to claim 11, wherein the processing means further comprises a first sampling circuit connected at an output of the processing circuit and operated to sample and store the output parameter (VAD) of the processing means.

13. The control device according to claim 6, wherein the driving means further comprises a protection circuit for the first electrolytic cell which prevents voltage at terminals of the first electrolytic cell from exceeding a specified threshold value, the protection circuit being operated by the operating unit.

14. The control device according to claim 2, wherein the controller comprises control means including measuring means for measuring internal resistance (RPVS) of the second electrolytic cell; the measuring means being operated by the operating unit to send a specified current to the second electrolytic cell whose strength can be regulated according to the type of the linear oxygen sensor which is connected to the controller.

15. The control device according to claim 14, wherein the measuring means comprises:

current generating means for generating the specified current in the second electrolytic cell;

third amplifier means connected to terminals of the second electrolytic cell for amplifying the voltage (DVS) at the terminals of the second electrolytic cell;

a second sampling circuit for sampling the amplified voltage (DVS); and timing means for synchronizing timing of the operations of sending the reference current and sampling the amplified voltage (DVS).

16. The control device according to claim 2, wherein the linear oxygen sensor further comprises a connector for connection to the controller, wherein the compensating resistance is connected between two terminals of the connector in two different ways according to the type of sensor which is connected to the controller; in a first way of the two different ways, corresponding to a first type of sensor, the compensating resistance is connected between a first and a second terminal, in a second way of the two different ways, corresponding to a second type of sensor, the compensating resistance is connected between the first terminal and a third terminal of the connector;

wherein the acquisition circuit comprises first and second means for acquiring the value (RCOMP; RCOMPDIFF) of the compensating resistance depending upon whether the compensating resistance is connected to the connector in the first way or in the second way, respectively.

17. The control device according to claim 16, wherein the first means for acquiring comprises a current generator circuit connected to the second terminal and operated by the operating unit to send a predetermined current to the compensating resistance; the first means for acquiring further comprising a differential amplifier having inputs connected to the first and second terminal to amplify voltage at terminals of the compensating resistance and to supply at the output a first voltage signal (RCOMPDIFF) indicating the value of the compensating resistance.

18. The control device according to claim 16, wherein the second means for acquiring comprises means for supplying a reference voltage (VBAT) to the third terminal and a voltage divider connected to the first terminal and generating a second voltage signal (RCOMP) at an output of the first terminal which indicates the value of the compensating resistance.

19. The control device according to claim 2, wherein the operating unit comprises a memory unit for permanently storing the value (RCOMP; RCOMPDIFF) of the compensating resistance so that the value (RCOMP; RCOMPDIFF) of the compensating resistance is available when the internal combustion engine is started.

20. The control device according to claim 1, wherein the operating unit and the controller comprise corresponding interface circuits of a serial type connected by a serial line; the operating unit sending operating and programming signals (SPI) of the programmable control means to the interface circuit of the controller.

* * * * *